(12) United States Patent
Baker et al.

(10) Patent No.: US 9,183,354 B2
(45) Date of Patent: Nov. 10, 2015

(54) SYSTEMS AND METHODS FOR IMAGE GUIDED SURGERY

(71) Applicants: MUSC FOUNDATION FOR RESEARCH DEVELOPMENT, Charleston, SC (US); Clemson University, Clemson, SC (US)

(72) Inventors: G. Hamilton Baker, Charleston, SC (US); David Kwartowitz, Pendleton, SC (US); Fuad Mefleh, Westminster, SC (US)

(73) Assignees: MUSC FOUNDATION FOR RESEARCH DEVELOPMENT, Charleston, SC (US); CLEMSON UNIVERSITY, Clemson, SC (US)

( * ) Notice: Subject to any disclaimer, the term of this patent is extended or adjusted under 35 U.S.C. 154(b) by 137 days.

(21) Appl. No.: 13/967,881

(22) Filed: Aug. 15, 2013

(65) Prior Publication Data

US 2014/0050375 A1   Feb. 20, 2014

Related U.S. Application Data

(60) Provisional application No. 61/683,386, filed on Aug. 15, 2012.

(51) Int. Cl.
*G06K 9/00* (2006.01)
*G06F 19/00* (2011.01)
(Continued)

(52) U.S. Cl.
CPC ........ *G06F 19/3481* (2013.01); *A61B 19/5244* (2013.01); *G06T 7/0042* (2013.01);
(Continued)

(58) Field of Classification Search
CPC .................................................. G06F 19/3481
See application file for complete search history.

(56) References Cited

U.S. PATENT DOCUMENTS 6,272,371 B1   8/2001 Shlomo
6,773,393 B1   8/2004 Taniguchi et al.
(Continued)

FOREIGN PATENT DOCUMENTS

EP   1521555   8/2009
EP   2105154   9/2009
(Continued)

OTHER PUBLICATIONS

Abi-Jaoudeh, N., et al., "Electromagnetic Navigation for Thoracic Aortic Stent Graft Deployment: A Pilot Study in Swine," *J Vasc Intery Radiol.*, Jun. 2010, vol. 21, No. 6, pp. 888-895.
(Continued)

*Primary Examiner* — Shefali Goradia
(74) *Attorney, Agent, or Firm* — Meunier Carlin & Curfman LLC

(57) ABSTRACT

Systems and methods for image guided surgery are disclosed herein. An example method can include: receiving a plurality of 2D projection images of an object at a plurality of projection angles during a first period of time; and receiving a position of an instrument relative to a tracking coordinate system during the first period of time. The method can also include registering the plurality of 2D projection images relative to the tracking coordinate system to obtain a transformation function that defines a relationship between a coordinate system of the plurality of 2D projection images and the tracking coordinate system; receiving an adjusted position of the instrument relative to the tracking coordinate system during a second period of time that is subsequent to the first period of time; and estimating an adjusted position of the instrument relative to the plurality of 2D projection images using the transformation function.

27 Claims, 6 Drawing Sheets

(51) Int. Cl.
*A61B 19/00* (2006.01)
*G06T 7/00* (2006.01)

(52) U.S. Cl.
CPC . *A61B2019/5238* (2013.01); *A61B 2019/5251* (2013.01); *A61B 2019/5289* (2013.01); *G06T 2207/10121* (2013.01); *G06T 2207/30048* (2013.01); *G06T 2207/30204* (2013.01)

(56) References Cited

U.S. PATENT DOCUMENTS

| | | | |
|---|---|---|---|
| 6,788,967 | B2 | 9/2004 | Ben-Haim et al. |
| 7,010,338 | B2 | 3/2006 | Ritter et al. |
| 7,195,587 | B2 | 3/2007 | Taniguchi et al. |
| 7,769,427 | B2 | 8/2010 | Shachar |
| 7,811,294 | B2 | 10/2010 | Strommer et al. |
| 7,824,328 | B2 | 11/2010 | Gattani et al. |
| 7,873,401 | B2 | 1/2011 | Shachar |
| 8,284,190 | B2 * | 10/2012 | Muktinutalapati et al. ... 345/419 |
| 8,526,700 | B2 * | 9/2013 | Isaacs ............... 382/131 |
| 8,908,943 | B2 * | 12/2014 | Berry et al. ............ 382/128 |
| 2004/0019447 | A1 | 1/2004 | Shachar |
| 2006/0114088 | A1 | 6/2006 | Shachar |
| 2006/0116634 | A1 | 6/2006 | Shachar |
| 2008/0125720 | A1 | 5/2008 | Kim et al. |
| 2008/0249395 | A1 | 10/2008 | Shachar et al. |
| 2012/0071753 | A1 | 3/2012 | Hunter et al. |
| 2013/0184567 | A1 | 7/2013 | Xie et al. |
| 2013/0216025 | A1 | 8/2013 | Chan et al. |
| 2013/0303893 | A1 | 11/2013 | Duindam et al. |
| 2013/0324833 | A1 | 12/2013 | Barley et al. |
| 2013/0325387 | A1 | 12/2013 | Manzke et al. |
| 2014/0022283 | A1 * | 1/2014 | Chan et al. ............ 345/633 |
| 2014/0039306 | A1 | 2/2014 | Klinder et al. |

FOREIGN PATENT DOCUMENTS

| | | |
|---|---|---|
| WO | 2004/006795 | 1/2004 |
| WO | 2007/067945 | 6/2007 |
| WO | 2013/083824 | 6/2013 |

OTHER PUBLICATIONS

Birkfellner, W., et al., "Systematic distortions in magnetic position digitizers," *Medical Physics*, vol. 25, pp. 2242-2248, Nov. 1998.

Eitel, C., et al., "EnSite Velocity™ cardiac mapping system: a new platform for 3D mapping of cardiac arrhythmias," *Expert Rev. Med. Devices*, vol. 7, No. 2, 2010, pp. 185-192.

Galloway, Jr., R. L. et al., "Interactive image-guided neurosurgery," *IEEE Trans Biomed Eng*, vol. 39, pp. 1226-1231, Dec. 1992.

Koolwal, A.B., et al., "Catheter localization in the left atrium using an outdated anatomic reference for guidance," *Conf Proc IEEE Eng Med Biol Soc.*, 2009, pp. 5567-5570.

"Medical Image Registration," 1-382 (Hajnal, J., et al. eds., CRC Press 2001).

Nazarian, S., et al., "Feasibility of Real-Time Magnetic Resonance Imaging for Catheter Guidance in Electrophysiology Studies," Circulation, *Journal of the American Heart Association*, 2008, vol. 118, No. 3, pp. 223-229.

Wagner, K., et al., "Quantitative analysis of factors affecting intraoperative precision and stability of optoelectronic and electromagnetic tracking systems," *Medical Physics*, vol. 29, pp. 905-912, May 2002.

Wood, B.J., et al., "Navigation with Electromagnetic Tracking for Interventional Radiology Procedures: A Feasibility Study," *J Vasc Interv Radiol.*, Apr. 2005, vol. 16, No. 4, pp. 493-505.

* cited by examiner

SYSTEMS AND METHODS FOR IMAGE GUIDED SURGERY

CROSS-REFERENCE TO RELATED APPLICATIONS

This application claims the benefit of U.S. Provisional Patent Application No. 61/683,386, filed on Aug. 15, 2012, entitled "SYSTEMS AND METHODS FOR IMAGE GUIDED SURGERY," the disclosure of which is expressly incorporated herein by reference in its entirety.

BACKGROUND

Radiation exposure from medical imaging has dramatically increased in recent decades. The average per capita radiation dose from medical imaging in the U.S. has increased six-fold over the last thirty years. This increase is of great concern to the public, medical community and regulatory agencies, and it has been identified as an important patient safety issue. Children have compounded risk associated with radiation exposure. The longer life expectancy of children as compared to adults provides a larger window of opportunity for expressing the damaging effects of ionizing radiation. In addition, epidemiologic studies of exposed populations demonstrated that children are considerably more sensitive to the carcinogenic effects of radiation.

Fluoroscopy, a form of medical radiation, is used to guide millions of medical procedures each year. For example, cardiac catheterizations are currently performed using fluoroscopy, which requires constant visualization of catheter manipulation by exposing the patient to ionizing radiation. While these important medical procedures can be lifesaving, the concomitant radiation exposure places the patient at risk for development of radiation-induced disease.

Children with congenital heart disease (CHD) are especially vulnerable. Many therapeutic interventions for CHD patients have transition from open surgical procedures to minimally invasive, catheter-based procedures requiring fluoroscopic guidance. While this trend has many benefits, it unfortunately results in excessive cumulative radiation exposure to children who often undergo multiple, complex catheter procedures. Moreover, recent studies in children with CHD who have undergone catheterization have demonstrated direct DNA evidence of long-lasting chromosomal damage. This alarming evidence underscores the need for an alternative to ionizing radiation to guide cardiac catheterizations in children.

To date, radiation dose reduction in cardiac catheterization has been aimed at modifying the existing technology to limit dose delivery. However, this approach is inherently limited because fluoroscopy remains the principal imaging modality.

SUMMARY

Systems and methods for image guided surgery are disclosed herein. The estimated position of an instrument relative to a plurality of projection images can be displayed to facilitate guidance of the instrument during the surgery. The systems and methods track the position of the instrument relative to a tracking coordinate system and estimate the position of the instrument relative to a coordinate system of the projection images. For example, the position of the instrument can be tracked using an electromagnetic (EM) tracking system, which uses a low-strength magnetic field to track the position of miniaturized sensor coils embedded in the instrument. EM tracking has been used as an adjunct modality for guiding certain types of interventional procedures. However, EM tracking has been limited to guiding procedure with respect to static reference images of a patient's anatomy (e.g., MRI, CT scan, etc.) acquired prior to the medical procedure. Using static reference images is a barrier to applying EM tracking for guidance of cardiology procedures because the dynamic nature of the heart renders the static reference images ineffective as an anatomic map. Thus, for EM tracking to be useful in interventional cardiology, the system should integrate real-time catheter position into a dynamic anatomical image of the heart.

An example method for guiding an instrument during a medical procedure can include: receiving a plurality of 2D projection images of an object at a plurality of projection angles; and receiving a position of the instrument relative to a tracking coordinate system. The plurality of 2D projection images can be recorded and the position of the instrument can be received during a first period of time. The method can also include registering the plurality of 2D projection images relative to the tracking coordinate system to obtain a transformation function that defines a relationship between a coordinate system of the plurality of 2D projection images and the tracking coordinate system; receiving an adjusted position of the instrument relative to the tracking coordinate system during a second period of time that is subsequent to the first period of time; and estimating an adjusted position of the instrument relative to the plurality of 2D projection images using the transformation function.

In some implementations, the method can include: continuously displaying the plurality of 2D projection images in a loop; and displaying the estimated adjusted position of the instrument relative to the plurality of 2D projection images on the loop.

Additionally, the plurality of 2D projection images can depict an actual position of the instrument relative to a patient's body during the first period of time.

In some implementations, the first period of time is approximately 3-5 seconds. It should be understood that the first period of time can be any length of time. For example, the first period of time can be long enough to provide an anatomic roadmap of the object for guidance during the procedure and short enough to reduce the amount of radiation exposure during the procedure.

Optionally, the method can include receiving a cine loop including a plurality of 2D projection images of an object at a plurality of projection angles. For example, the cine loop can be recorded by an imaging system. The cine loop can optionally be recorded prior to performing the medical procedure.

Additionally, registering the plurality of 2D projection images relative to the tracking coordinate system to obtain a transformation function according to the implementations discussed above can include: receiving a position of the instrument relative to the tracking coordinate system at each of a plurality of fiducial markers; identifying a corresponding position of each of the plurality of fiducial markers in at least one of the plurality of 2D projection images; and performing a point-based algorithm based on the position of the instrument relative to the tracking coordinate system at each of the plurality of fiducial markers and the corresponding position of each of the plurality of fiducial markers in the at least one of the plurality of 2D projection images to obtain the transformation function. The fiducial markers can be known points (e.g., anatomic landmarks) in both the 2D projection images and the physical space. In some implementations, the point-based algorithm includes performing a least squares fit based on a number of the plurality of fiducial markers.

Alternatively, in other implementations, registering the plurality of 2D projection images relative to the tracking coordinate system to obtain a transformation function can include: identifying a surface feature of the object relative to the tracking coordinate system; identifying a corresponding surface feature of the object in at least one of the plurality of 2D projection images; and performing a surface-matching algorithm based on the surface feature relative to the tracking coordinate system and the corresponding surface feature in the at least one of the plurality of 2D projection images to obtain the transformation function.

In yet other implementations, registering the plurality of 2D projection images relative to the tracking coordinate system to obtain a transformation function can include: identifying a volume feature of the object relative to the tracking coordinate system; identifying a corresponding volume feature of the object in at least one of the plurality of 2D projection images; and performing a volume-matching algorithm based on the volume feature relative to the tracking coordinate system and the corresponding volume feature of the object in at least one of the plurality of 2D projection images to obtain the transformation function.

In some implementations, the object is subject to periodic movement. For example, the object can be a patient's organ such as the patient's heart.

In response to detecting patient movement during the medical procedure, the method can further include: receiving a plurality of updated 2D projection images of the object at a plurality of projection angles during a third period of time; and registering the plurality of updated 2D projection images relative to the tracking coordinate system to obtain an updated transformation function that defines a relationship between a coordinate system of the plurality of updated 2D projection images and the tracking coordinate system. Optionally, the method can include continuously displaying the plurality of updated 2D projection images in an updated loop; receiving an adjusted position of the instrument relative to the tracking coordinate system during a fourth period of time that is subsequent to the third period of time; estimating an adjusted position of the instrument relative to the plurality of updated 2D projection images using the updated transformation function; and displaying the estimated adjusted position of the instrument relative to the plurality of 2D projection images on the updated loop.

In other implementations, registering the plurality of 2D projection images relative to the tracking coordinate system to obtain a transformation function can include: creating a 3D model image of at least a portion of the object based on the plurality of 2D projection images; and registering the 3D model image relative to the tracking coordinate system to obtain a transformation function that defines a relationship between a coordinate system of the 3D model image and the tracking coordinate system. In these implementations, estimating an adjusted position of the instrument can include estimating an adjusted position of the instrument relative to the 3D model image using the transformation function. The method can also include: continuously displaying the 3D model image in a loop; and displaying the estimated adjusted position of the instrument relative to the 3D model image on the loop.

In some implementations, the plurality of 2D projection images can be biplane fluoroscopic images. Additionally, the plurality of projection angles can include lateral and AP projections.

In other implementations, the plurality of 2D projection images can be ultrasound images.

Optionally, the method can include: detecting the position of the instrument by sensing a change in a magnetic field; and determining the position of the instrument relative to the tracking coordinate system of the magnetic field.

Alternatively, the method can optionally include: receiving a signal from the instrument at an optical sensor; and determining the position of the instrument relative to the tracking coordinate system of the optical sensor.

In the implementations discussed above, the instrument can be a catheter. Additionally, the medical procedure can be an interventional cardiology procedure such as a valvuloplasty, an angioplasty, delivery of an occlusion device, a valve replacement, an atrial septostomy and a Fontan procedure.

It should be understood that the above-described subject matter may also be implemented as a computer-controlled apparatus, a computer process, a computing system, an article of manufacture, such as a computer-readable storage medium, or a system.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a", "an", "the", include plural referents unless the context clearly dictates otherwise. The term "comprising" and variations thereof as used herein is used synonymously with the term "including" and variations thereof and are open, non-limiting terms. While implementations will be described for guiding a surgical instrument during a surgical procedure such as an interventional cardiology procedure, it will become evident to those skilled in the art that the implementations are not limited thereto. For example, it should be understood that the implementations described herein are applicable for guiding a surgical instrument during other types of surgical procedures.

Figure 1:
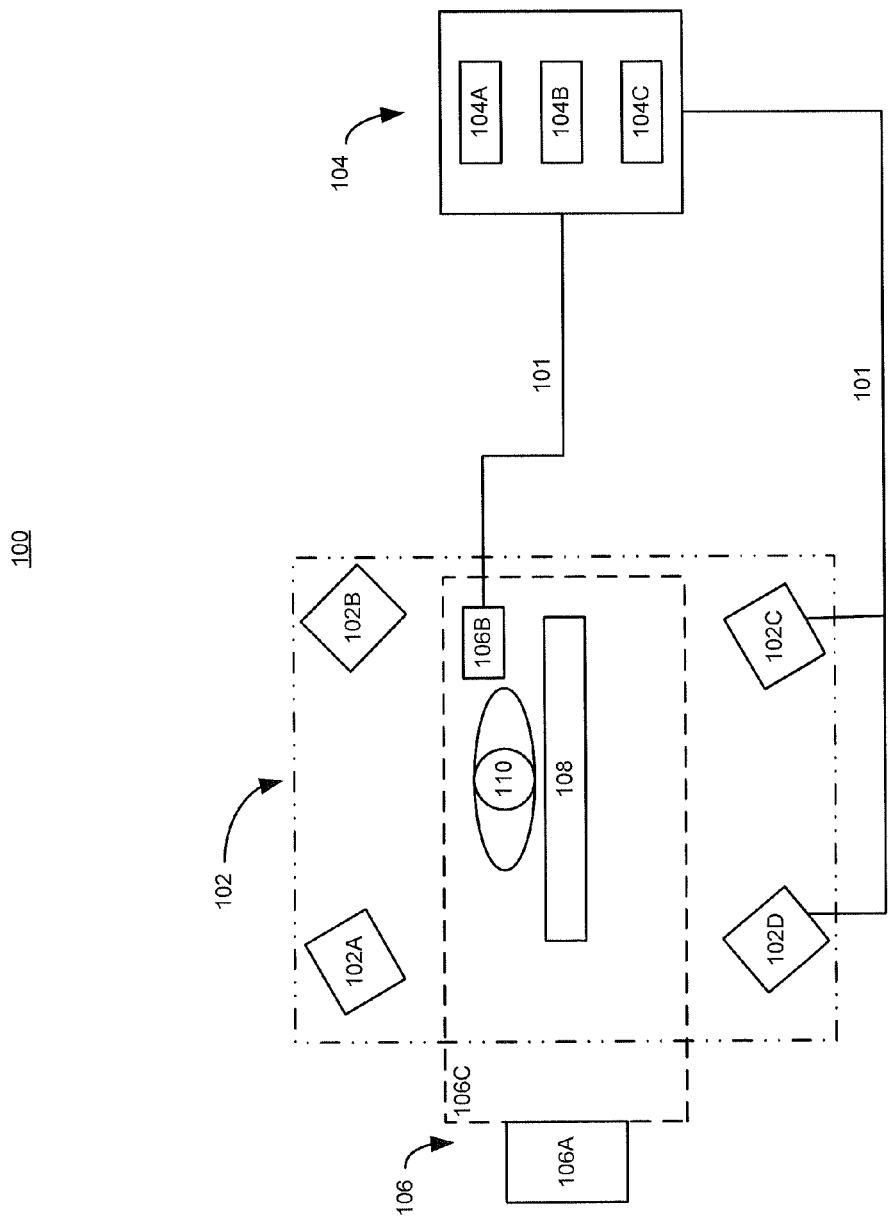
FIG. 1 is a block diagram illustrating an image guidance system according to an example implementation discussed herein.

Referring now to FIG. 1, an example image guidance system (IGS) 100 is shown. The IGS 100 can include an imaging system 102, a guidance computing device 104 and an instrument tracking system 106. The IGS 100 can be used guide an instrument during a medical procedure performed on a patient 110. It should be understood that the subject patient discussed herein can be human and non-human mammals of any age. The imaging system 102 can be an x-ray system, an ultrasound system, or other type of imaging system. The imaging system 102 is capable of imaging (or capturing, recording, etc.) a plurality of 2D projection images of an object at a plurality of projection angles. In the implementations discussed below, the projection angle of each of the 2D projection images can be different. For example, the imaging system 102 can be a biplane fluoroscopic imaging system, which is capable of imaging two perpendicular image planes. Additionally, the imaging system 102 can optionally be a flat-panel biplane fluoroscopic imaging system. A flat-panel biplane fluoroscopic imaging system eliminates the image intensifier. A biplane fluoroscopic imaging system is capable of imaging the XZ plane (i.e., a lateral view) and the YZ plane (i.e., an AP view). It should be understood that the image planes are not limited to the XZ and YZ planes and that the image planes can be any two or more image planes. In a biplane fluoroscopic image, the Z extent along the length of the imaged object is present in both perpendicular image planes, which results in a 4D image of a 3D space (i.e., an over-determined problem exists).

As shown in FIG. 1, the imaging system 102 includes x-ray sources 102A, 102B and corresponding x-ray detectors 102C, 102D for imaging the at least two image planes. For example, x-ray source 102A and corresponding x-ray detector 102C can image the XZ plane, and x-ray source 102B and corresponding x-ray detector 102D can image the YZ plane. Although not shown in FIG. 1, the x-ray source 102A and the x-ray detector 102C, as well as the x-ray source 102B in the x-ray detector 102D, can be fixed to a C-arm, for example. Thus, the angular position of each C-arm can be varied around a bed 108 on which the patient 110 is supported in order to obtain images at different projection angles. The 2D projection images can be communicated from the imaging system 102 over a communication link 101 to the guidance computing device 104. This disclosure contemplates the communication link is any suitable communication link. For example, a communication link may be implemented by any medium that facilitates data exchange between the imaging system 102 and the guidance computing device 104 including, but not limited to, wired, wireless and optical links. It should be understood that the imaging system 102 is not limited to a biplane fluoroscopic imaging system. For example, the imaging system 102 can be any type of imaging system capable of imaging a plurality of 2D projection images of an object at a plurality of projection angles such as a 3D echocardiography system.

The IGS 100 can also include an instrument tracking system 106. In some implementations, the instrument tracking system 106 can be an EM tracking system. An EM tracking system is capable of tracking the position of the instrument relative to a tracking coordinate system using a low-intensity, varying EM field. As used herein, the position of the instrument is the position of the instrument relative to a coordinate system or the position and orientation of the instrument relative to the coordinate system. An example EM tracking system that can be used in the implementations discussed herein is the AURORA EM TRACKING SYSTEM of NORTHERN DIGITAL, INC. (NDI), WATERLOO, ONTARIO, CANADA. In other implementations, the instrument tracking system 106 can be an optical tracking system. In an optical tracking system, the position of the instrument can be tracked with regard to a tracking coordinate system by detecting signals (e.g., infrared light) emitted or reflected from markers embedded in the instrument. As shown in FIG. 1, the instrument tracking system 106 can include a magnetic field generator 106A that is capable of producing a low-intensity, varying EM field 106C around the patient 110. An instrument such as a catheter, for example, can include one or more sensors 106B such as sensor coils. The sensors 102B can optionally be 6-degree-of-freedom (DOF) sensors (or other x-DOF sensors such as 5-DOF sensors, for example) embedded in the instrument to allow validation of position, shape and orientation of the instrument. By varying the EM field 106C, currents (i.e., electrical signals) are induced in the sensors 106B of the instrument. The characteristics of the electrical signals depend on the distance and angle between the sensors 106B of the instrument and the magnetic field generator 106A. Additionally, the electrical signals can be communicated from the instrument tracking system 106 over a communication link 101 to the guidance computing device 104. As discussed above, a communication link may be implemented by any medium that facilitates data exchange between the instrument tracking system 106 and the guidance computing device 104 including, but not limited to, wired, wireless and optical links. Using the instrument tracking system 106, it is possible to sense a change in the EM field with the sensors 106B and then determine the position of the instrument relative to a tracking coordinate system of the EM field 106C. It should be understood that the instrument tracking system 106 is not limited to an EM tracking system or an optical tracking system and can be another type of system for tracking the position of the instrument.

As discussed above, the plurality of 2D projection images captured by the imaging system 102 and the electrical signals detected by the instrument tracking system 106 are communicated to the guidance computing device 104. As shown in FIG. 1, the guidance computing device 104 includes a display unit 104A, a processing unit 104B and a memory 104C. As discussed in detail below, it is possible to program the guidance computing device 104 to estimate the position of the instrument (e.g., a catheter), which is tracked using the instrument tracking system 106, relative to the plurality of 2D projection images imaged with the imaging system 102 and then display the estimated position of the instrument relative to the plurality of 2D projection images on the display unit 104A. To estimate the position of the instrument relative to the plurality of 2D projection images, the tracking coordinate system and the coordinate system of the 2D projection images are correlated via a transformation function in a process known as registration. It should be understood that there are a number of known methods for performing registration between the coordinate systems. For example, the 2D projection images can be registered relative to the tracking coordinate system to obtain the transformation function that defines a relationship between the 2D coordinate system of the 2D projection images and the 3D coordinate system of the tracking coordinate system (e.g., 2D-3D registration) using a point-based algorithm. In a point-based algorithm, corresponding points in each of the coordinate systems are identified, the identified points are registered and the transformation function is then inferred.

For example, fiducial markers or anatomic landmarks (e.g., known points) in the 2D projection images and the physical space can be used for the registration. The position of the fiducial markers in a coordinate system of the 2D projection images can be identified based on at least one of the 2D projection images. Additionally, the instrument can be manipulated/moved to each of the fiducial makers in the physical space such that the position of the instrument relative to the tracking coordinate system at each of the fiducial markers is detected (i.e., by the instrument tracking system 106). Then, a closed form least squares fit based on the number of fiducial markers can be performed (i.e., a Procrustes analysis) to obtain the transformation function. As discussed above, the transformation function defines the relationship between the coordinate system of the 2D projection images and the tracking coordinate system. When registering biplane fluoroscopic images relative to the tracking coordinate system, each of the 2D projection images can be registered with the tracking coordinate system. In other words, a 2D-3D registration can be performed on each of the 2D projection images and the tracking coordinate system. It should be understood that the point-based algorithm discussed above is only one example algorithm and that other algorithms (point-based or otherwise) exist. For example, it is possible to obtain the transformation function using surface or volume methods, which will allow for a personalized fit between the 2D dimensional projection images and the physical space without requiring additional fiducial markers or anatomic landmarks. When using surface or volume methods, corresponding surface or volume features are identified in the 2D projection images and the physical space. For example, a surface feature can be identified in the physical space by swabbing a surface (e.g., a heart wall) with the instrument that is tracked using the instrument tracking system 106. Then, a surface-matching or volume-matching algorithm is used to obtain the transformation function.

Alternatively to performing 2D-3D registration between the 2D projection images and the tracking coordinate system, it is possible to create a 3D model image of at least a portion of an object captured in the plurality of 2D projection images, and perform 3D-3D registration between a 3D coordinate system of the 3D model image and the tracking coordinate system. It should be understood that there are a number of methods for creating the 3D model image from at least two 2D projection images captured at different projection angles. In some implementations, a 3D model image of a patient's organ (e.g., the heart) can be constructed based on the plurality of 2D projection images such as biplane fluoroscopic images or ultrasound images. This disclosure contemplates that a 3D model image of other organs can be created and that the disclosure should not be limited to 3D model images of the patient's heart, which is only one example. Similarly to the processes discussed above with regard to 2D-3D registration, 3D-3D registration can be performed between the coordinate system of the 3D model image and the tracking coordinate system using point-based, surface-based or volume-based algorithms to obtain a transformation function relating the coordinate systems.

Using the IGS 100, it is possible to reduce, and in some cases eliminate, radiation exposure during a medical procedure such as an interventional cardiology procedure. For example, the interventional cardiology procedure can optionally include, but is not limited to: valvuloplasty (e.g., mitral, aortic, pulmonary, and/or tricuspid valvuloplasty); pulmonary artery angioplasty with/without stent implantation; right ventricle to pulmonary artery conduit angioplasty with/without stent implantation; Blalock-Taussig (or other surgical shunt) angioplasty with/without stent implantation; angioplasty of aortic coarctation with/without stent implantation; angioplasty of systemic venous obstruction with/without stent implantation; delivery of atrial septal defect occlusion devices; delivery of patent ductus arteriousus occlusion devices; delivery of ventricular septal defect occlusion devices; percutaneous valve replacement (e.g., mitral, aortic, pulmonary, and/or tricuspid percutaneous valve replacement); atrial transeptal puncture balloon atrial septostomy; occlusion of detrimental collateral vessels (e.g., systemic to pulmonary arterial vessels, arteriovenous malformations, veno-venous collaterals); percutaneous closure of Fontan fenestrations and percutaneous creation of Fontan fenestrations. The object can be imaged with the imaging system 102 at the plurality of projection angles. The imaging system 102 can be a fluoroscopic imaging system, an ultrasound imaging system or other type of imaging system. It should be understood that the IGS 100 according to implementations discussed herein including an imaging system using radiation (e.g., a fluoroscopic imaging system) can reduce radiation exposure, while the IGS 100 including an imaging system not using radiation (e.g., an ultrasound imaging system) can eliminate radiation exposure. The object can be subject to periodic movement. In some implementations, the object is a patient's organ such as the patient's heart, which is subject to periodic movement. The plurality of 2D projection images can be captured during a first period of time. The first period of time can be a fixed period of time. For example, the first period of time can be approximately 3-5 seconds. It should be understood, however, that the first period of time can be any length of time. Optionally, the 2D projection images recorded during the first period of time can be a cine loop (i.e., a sequence of 2D projection images recorded during the first period of time). Optionally, the first period of time can be prior to performing the medical procedure. Alternatively or additionally, the plurality of 2D projection images can optionally be captured by a medical professional (e.g., a surgeon) using a foot pedal to operate the imaging system, which provides for hands-free control. Additionally, in some implementations, the 2D projection images can depict an actual position of the instrument relative to the patient's body during the first period of time.

As discussed above, prolonged radiation exposure during a medical procedure such as a cardiac catheterization, especially in children, can have long-term negative effects. For example, the fluoroscopy time during a simple cardiac procedure is typically about 5 minutes, while the fluoroscopy time during an interventional cardiac procedure is typically about 20 minutes. However, using the IGS 100, it is possible to reduce exposure to radiation by estimating and displaying the position of the instrument relative to the 2D projection images, which were captured during the first period of time. The first period of time can be substantially less than typical fluoroscopic imaging times during conventional procedures. In some implementations, the plurality of 2D projection images can be displayed continuously in a loop. In other words, the plurality of 2D projection images captured during the first period of time (e.g., a 3-5 second period) can be continuously replayed during the medical procedure without exposing the patient to additional radiation. The adjusted position of the instrument can be tracked during the medical procedure relative to the tracking coordinate system using the instrument tracking system 106. The adjusted position of the instrument can then be tracked during the medical procedure in a second period of time that is subsequent to the first period of time. Then, using the previously-obtained transformation function, the adjusted position of the instrument relative to the 2D projection images can be estimated. Optionally, the estimated adjusted position of the instrument relative to the 2D projection images can be displayed, for example, on the loop.

The instrument can be navigated during the medical procedure using the IGS 100 because the plurality of 2D projection images captured during the first time period and displayed continuously in a loop serve as a dynamic anatomical roadmap. Additionally, because the patient lies motionless during the medical procedure such as an interventional cardiac procedure, the accuracy of repeating the loop as an anatomic map is preserved. Further, even if unexpected patient motion occurs, a plurality of updated 2D projection images of the object at a plurality of projection angles can be recorded using the imaging system 102. The updated 2D projection images can be recorded during a third period of time, for example, which can be substantially less than typical fluoroscopic imaging times during conventional procedures (e.g., 3-5 seconds). Then, in accordance with the processes discussed above, the updated 2D projection images can be registered relative to the tracking coordinate system to obtain an updated transformation function. Thereafter, the adjusted position of the instrument during a fourth period of time subsequent to the third period of time can be estimated using the updated transformation function and displayed relative to the updated 2D projection images, which are continuously displayed in a loop. Thus, using the IGS 100, the patient is exposed to a fraction of the radiation the patient would have been exposed to during a conventional medical procedure when the IGS 100 includes an imaging system using radiation, and the patient is not exposed to radiation when the IGS 100 includes an imaging system that does not use radiation.

Figure 2:
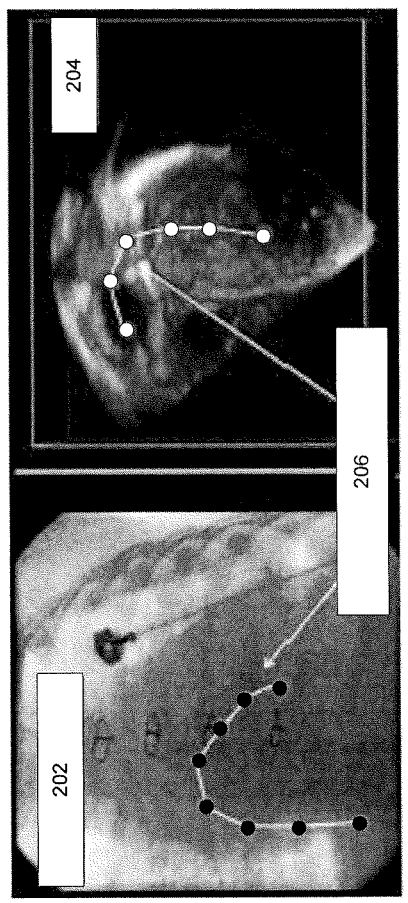
FIGS. 2A-2B are example images illustrating instrument positions according to example implementations discussed herein.

Referring now to FIGS. 2A-2B, example images illustrating instrument positions are shown. FIG. 2A is an image illustrating a position of the instrument 206 (e.g., a catheter) on a fluoroscopic loop 202. As discussed above, the position of the instrument is tracked using the instrument tracking system 106. Using the transformation function, it is possible to estimate the position of the instrument relative to the plurality of 2D projection images (e.g., a fluoroscopic loop). The position of the instrument 206 can then be displayed on the fluoroscopic loop 202. Additionally, FIG. 2B is an image illustrating the position of the instrument 206 (e.g., a catheter) on a 3D echocardiogram 204. Unlike static reference images, the fluoroscopic loop 202 and the 3D echocardiogram can act as dynamic anatomic roadmaps for performing image guided surgery.

Conventionally, instrument tracking systems (e.g., KNIFE) typically provide for tracking and display of the tip of an instrument (e.g., a catheter) during the medical procedure. In other words, a sensor (e.g., sensor 106B of FIG. 1) that is tracked by the instrument tracking system (e.g., instrument tracking system 106 of FIG. 1) is provided only in the tip of the catheter. It should be understood that a catheter is provided only as one example of the instrument and that the instrument should not be limited to a catheter. However, because the catheter can bend at one or more points along its extent, the exact shape and pose of the catheter cannot be determined using the instrument tracking system alone. Instead, a medical imaging technique such as fluoroscopy is used to display the shape and pose of the catheter, which allows for easier navigation during the medical procedure. Using fluoroscopy to guide the catheter, however, increases the patient's exposure to radiation. This is undesirable in a number of circumstances.

Figure 5:
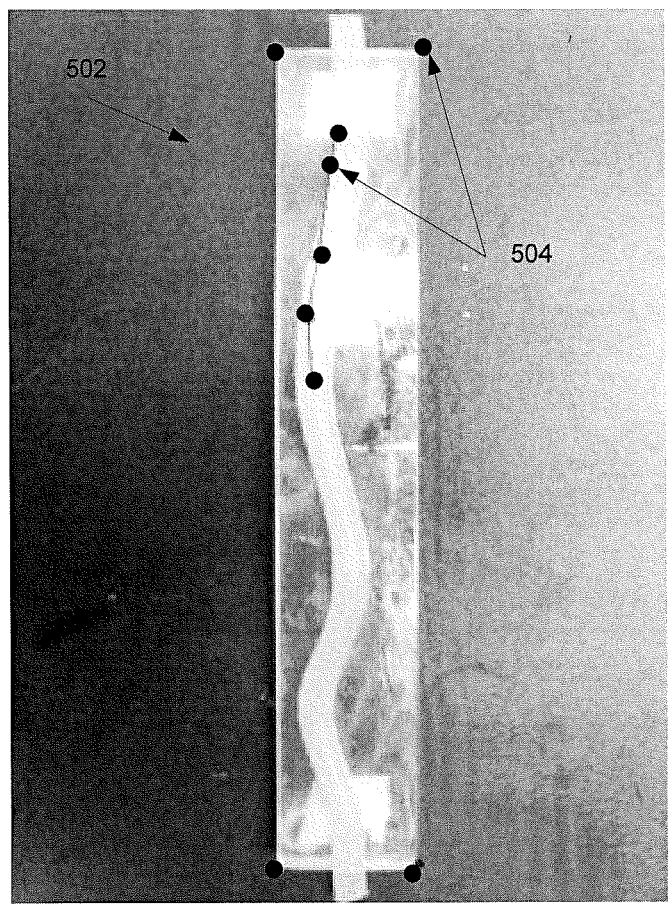
FIG. 5 is an example of a catheter shape rendering estimated by tracking a plurality of sensors in the catheter with an image tracking system.

As described above, the instrument (e.g., a catheter) can include one or more sensors (e.g., sensors 106B in FIG. 1) that can be tracked using an instrument tracking system (e.g., instrument tracking system 106 in FIG. 1). Thus, in some implementations, the instrument can optionally include a plurality of sensors arranged along the extent of the instrument. For example, when the instrument is a catheter, the sensors can be provided along the entire extent of the catheter (as opposed to only at a tip of the catheter), for example, at varying intervals along the extent of the catheter. This disclosure contemplates that the number of sensors can be selected to allow the shape and pose of the catheter to be estimated, in addition to tracking the position of the catheter, during the medical procedure while minimizing the number of sensors. By providing catheter shape and pose information, for example, in the form of an overlay on the 2D projection images (e.g., the fluoroscopic loop), it is possible to provide the clinician with the benefits of fluoroscopic catheter guidance but without exposing the patient to additional radiation. FIG. 5 is an example of a catheter shape rendering 502 estimated by tracking a plurality of sensors 504 in the catheter with an image tracking system.

By tracking the position of a plurality of sensors in the catheter using the instrument tracking system, the shape and pose of the catheter can be estimated during the medical procedure. By estimating the shape and pose of the catheter, it is possible to display the shape of the catheter, as well as the direction and angle of the catheter tip during the medical procedure. It should be understood that the location of each of the plurality of sensors within the catheter is known. Additionally, images (e.g., x-ray images) of the catheter can be captured. By comparing the shape of the catheter captured in the images and the tracked positions of each of the plurality of sensors, an algorithm for estimating the shape and pose of the catheter can be determined. Alternatively or additionally, 2D directional vectors of the catheter can be determined using the tracked position and orientation of each of the plurality of sensors of the catheter. This information can be used to allow a clinician to guide the catheter during the medical procedure using an overlay of the directional information on an image (e.g., an x-ray or an ultrasound image), even using a single plane fluoroscopy image.

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 3:
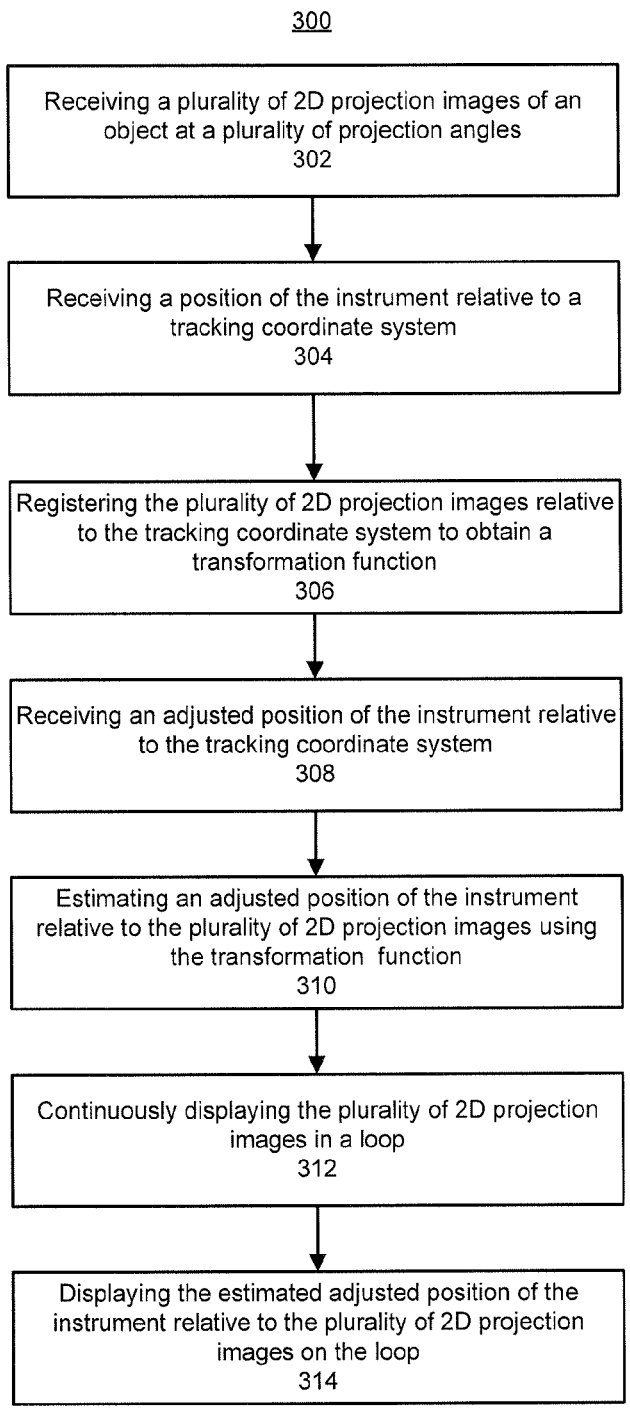
FIG. 3 is a flow diagram illustrating example operations for guiding an instrument using the image guidance system of FIG. 1.

Referring now to FIG. 3, a flow diagram illustrating example operations 300 for guiding an instrument using the image guidance system of FIG. 1 is shown. At 302, a plurality of 2D projection images of an object at a plurality of projection angles can be received. For example, the 2D projection images can be captured by the imaging system 102 and communicated to the guidance computing device 104 as discussed above. In some implementations, the 2D projection images are captured during a first period of time, which can be substantially less than typical fluoroscopic imaging times during conventional procedures. At 304, a position of the instrument relative to a tracking coordinate system is received. The position of the instrument can be detected by the instrument tracking system 106 and communicated to the guidance computing device 104 as discussed above. Then, at 306, the plurality of 2D projection images can be registered relative to the tracking coordinate system to obtain a transformation function that defines a relationship between a coordinate system of the plurality of 2D projection images and the tracking coordinate system. It should be understood that there are a number of algorithms for registering the coordinate systems. After obtaining the transformation function, an adjusted position of the instrument relative to the tracking coordinate system is received at 308. The adjusted position of the instrument can be received during a second period of time that is subsequent to the first period. At 310, an adjusted position of the instrument relative to the plurality of 2D projection images can be estimated using the transformation function. Optionally, at 312, the plurality of 2D projection images can be continuously displayed in a loop. For example, the 2D projection images can be captured during the first period of time (e.g., a 3-5 second period) and continuously replayed/displayed in a loop. Thereafter, the estimated adjusted position of the instrument relative to the plurality of 2D projection images can be displayed on the loop at 314 to guide the surgery.

Figure 4:
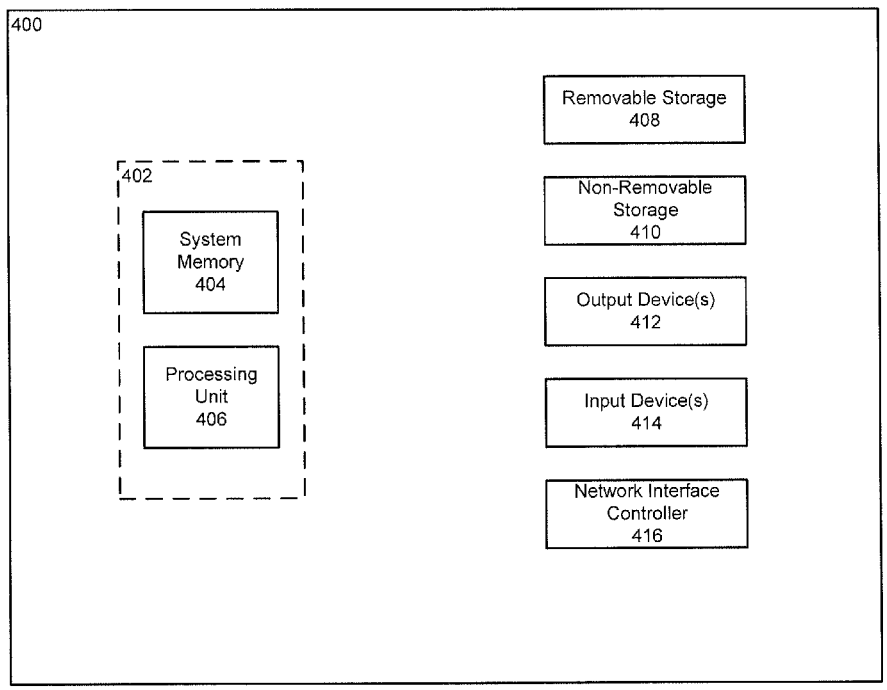
FIG. 4 is a block diagram illustrating an example computing device.

When the logical operations described herein are implemented in software, the process may execute on any type of computing architecture or platform. For example, referring to FIG. 4, an example computing device upon which embodiments of the invention may be implemented is illustrated. In particular, the computing device and/or the guidance computing device 104 discussed above may be a computing device, such as computing device 400 shown in FIG. 4. The computing device 400 may include a bus or other communication mechanism for communicating information among various components of the computing device 400. In its most basic configuration, computing device 400 typically includes at least one processing unit 406 and system memory 404. Depending on the exact configuration and type of computing device, system memory 404 may be volatile (such as random access memory (RAM)), non-volatile (such as read-only memory (ROM), flash memory, etc.), or some combination of the two. This most basic configuration is illustrated in FIG. 4 by dashed line 402. The processing unit 406 may be a standard programmable processor that performs arithmetic and logic operations necessary for operation of the computing device 400.

Computing device 400 may have additional features/functionality. For example, computing device 400 may include additional storage such as removable storage 408 and non-removable storage 410 including, but not limited to, magnetic or optical disks or tapes. Computing device 400 may also contain network connection(s) 416 that allow the device to communicate with other devices. Computing device 400 may also have input device(s) 414 such as a keyboard, mouse, touch screen, etc. Output device(s) 412 such as a display, speakers, printer, etc. may also be included. The additional devices may be connected to the bus in order to facilitate communication of data among the components of the computing device 400. All these devices are well known in the art and need not be discussed at length here.

The processing unit 406 may be configured to execute program code encoded in tangible, computer-readable media (or non-transitory computer-readable media). Computer-readable media refers to any media that is capable of providing data that causes the computing device 400 (i.e., a machine) to operate in a particular fashion. Various computer-readable media may be utilized to provide instructions to the processing unit 406 for execution. Common forms of computer-readable media include, for example, magnetic media, optical media, physical media, memory chips or cartridges, a carrier wave, or any other medium from which a computer can read. Example computer-readable media may include, but is not limited to, volatile media, non-volatile media and transmission media. Volatile and non-volatile media may be implemented in any method or technology for storage of information such as computer readable instructions, data structures, program modules or other data and common forms are discussed in detail below. Transmission media may include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 406 may execute program code stored in the system memory 404. For example, the bus may carry data to the system memory 404, from which the processing unit 406 receives and executes instructions. The data received by the system memory 404 may optionally be stored on the removable storage 408 or the non-removable storage 410 before or after execution by the processing unit 406.

Computing device 400 typically includes a variety of computer-readable media. Computer-readable media can be any available media that can be accessed by device 400 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 404, removable storage 408, and non-removable storage 410 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 400. Any such computer storage media may be part of computing device 400.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Examples

Intrinsic parameters of a fluoroscope, e.g., principal point (u0, v0) and focal length (f), can be estimated using an automated calibration technique. The example automated calibration technique described herein used fluoroscopic images of a 3D grid phantom built with known geometric constraints. For example, the 3D grid phantom was constructed through the layering of several 10 cm×10 cm×0.3 cm acrylic sheets, each sheet containing a different hole pattern cut by a laser-milling machine (i.e., VERSALASER 2.30, 145 from UNIVERSAL LASER SYSTEMS, INC. of SCOTTSDALE, Ariz.). Lead BBs were placed in the holes at each layer to serve as markers for the calibration. Overall, the design generated a 3D phantom with markers at varying locations in all three planes allowing for constrained volumetric marker capture of the fluoroscopic imaging volume. The phantom was imaged using a TOSHIBA BI-PLANE INFINIX-I SERIES fluoroscope with solid-state detectors from TOSHIBA, INC. of TAWARA-SHI, TOCHIGI-KEN, JAPAN and a ZIEHM IMAGING II C-ARM from ZIEHM IMAGING of ORLANDO, Fla. The fluoroscopic images were captured with the 3D phantom oriented to face the x-ray source in both the anterior-posterior (AP) and lateral (LR) planes for the bi-plane fluoroscope. Position of the 3D phantom relative to the x-ray source and detector were recorded along with the captured fluoroscopic images.

Figure 6:
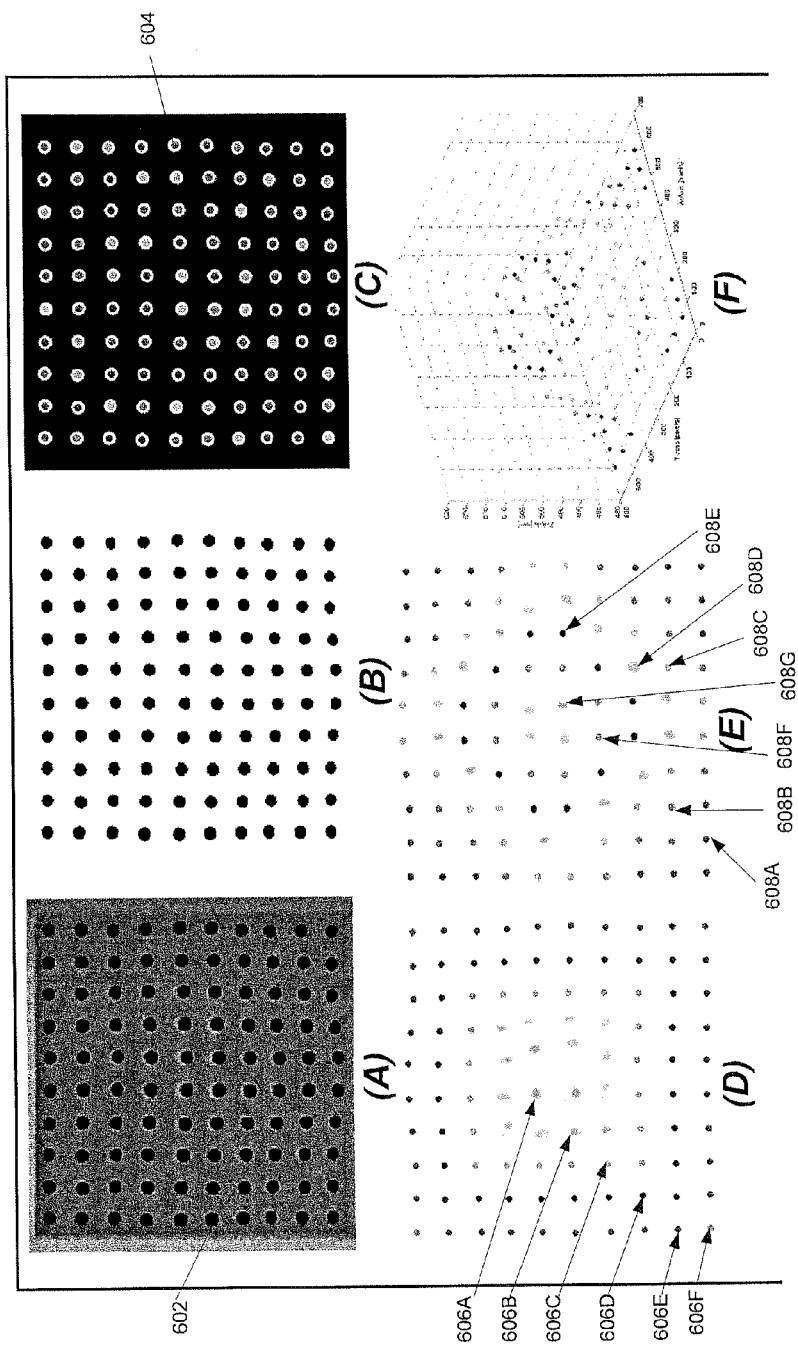
FIGS. 6A-6E are example images obtained while performing an automated estimation of fluoroscopic intrinsic parameters.
FIG. 6F is a graph illustrating a 3D plot of centroids extracted from a fluoroscopic image.

The example automated calibration of the fluoroscope used the captured fluoroscopic images, recorded distances and the geometric design of the 3D phantom. FIG. 6A is the original fluoroscopic image. Because each marker (e.g., lead BB) completely attenuates the x-ray beam, the markers 602 are represented as dark circles on the captured image in FIG. 6A. A binary mask was then created using a threshold value 5% lower than the maximum pixel value of the markers 602 in FIG. 6A. The binary mask is shown in FIG. 6B. Connected-component labeling was then used for the 160 detections of the individual markers in the fluoroscopic image, and the gray weighted centroid 604 of each located marker was calculated. FIG. 6C illustrates the connected-component labels of the markers 602 in FIG. 6A. Each marker was then assigned a location identifier 606A-606F based on its location in the 3D phantom, which is shown in FIG. 6D. The location identifiers were assigned based on the calculated neighbor count of each marker, as well the location identifier of those neighbors. Different colors were applied to signify different location assignments in FIG. 6D. In other words, the color assigned to marker 606A is different than the color assigned to each of markers 606B, 606C, 606D, 606E and 606F. Additionally, each centroid location was then given a depth 608A-608G based on the assigned location identifiers and the recorded distance from the x-ray source, which is shown in FIG. 6E. Similar to FIG. 6D, different colors were applied to signify different depths in FIG. 6E. In other words, the color assigned to marker 608A is different than the color assigned to each of markers 608B, 608C, 608D, 608E, 608F and 608G.

Equations for the finding the pixel location in perspective imaging are provided below:

$$u = f\frac{X}{Z} + u_0 \quad (1)$$

$$v = -f\frac{Y}{Z} + v_0 \quad (2)$$

In Eqns. (1) and (2), (u, v) is the image point in pixels and (X, Y, Z) is the camera point in millimeters. Since the true values for X and Y are unknown for each point, relative distances from other points can be used in determining the principal point (u0, v0) and focal length (f) of the fluoroscope.

Assuming the marker in the top-left corner of the 3D phantom to be the origin, distances for each marker from the origin were found. Utilizing the calculated distances from the origin, Dx and Dy, in the x and y direction respectively, the following sets of equations were used to find the fluoroscopic parameters using a multivariate linear regression in which the equation for each marker-origin pair was used.

$$Y_{(0,0)} = Y_{(n,n)} + D_y \quad (3)$$

$$X_{(0,0)} = X_{(n,n)} + D_x \quad (4)$$

$$Y_{(n,n)} = \frac{Z_{(n,n)}}{f}[(v_0 - v_{(n,n)})s_y] \quad (5)$$

$$X_{(n,n)} = \frac{Z_{(n,n)}}{f}[(u_{(n,n)} - u_0)s_x] \quad (6)$$

Eqns. (3) and (4) were used to find the location of an adjacent point in both the x and y axes, respectively. Locations of points can also be found using Eqns. (5) and (6). By substituting Eqns. (5) and (6) into Eqns. (3) and (4), a general form to calculate the unknown intrinsic parameters of the fluoroscope can be derived.

$$D_x f - s_x u_0(Z_{(n,n)} - Z_{(0,0)}) = s_x(Z_{(0,0)}u_{(0,0)} - Z_{(n,n)}u_{(n,n)}) \quad (7)$$

$$D_y f - s_y v_0(Z_{(0,0)} - Z_{(n,n)}) = s_y(Z_{(n,n)}u_{(n,n)} - Z_{(0,0)}u_{(0,0)}) \quad (8)$$

Eqns. (7) and (8) were populated and used in the multivariate linear regression to find the maximum likelihood estimation of the fluoroscopic intrinsic parameters.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for guiding an instrument during a medical procedure, comprising:
   receiving a plurality of 2D projection images of an object at a plurality of projection angles, the plurality of 2D projection images being recorded during a first period of time;
   receiving a position of the instrument relative to a tracking coordinate system during the first period of time;

registering the plurality of 2D projection images relative to the tracking coordinate system to obtain a transformation function that defines a relationship between a coordinate system of the plurality of 2D projection images and the tracking coordinate system;

receiving an adjusted position of the instrument relative to the tracking coordinate system during a second period of time that is subsequent to the first period of time; and estimating an adjusted position of the instrument relative to the plurality of 2D projection images using the transformation function.

2. The method of claim 1, further comprising:
continuously displaying the plurality of 2D projection images in a loop; and
displaying the estimated adjusted position of the instrument relative to the plurality of 2D projection images on the loop.

3. The method of claim 1, wherein the plurality of 2D projection images depict an actual position of the instrument relative to a patient's body during the first period of time.

4. The method of claim 1, further comprising recording a cine loop including the plurality of 2D projection images of the object at the plurality of projection angles, wherein the cine loop is recorded prior to performing the medical procedure.

5. The method of claim 1, wherein registering the plurality of 2D projection images relative to the tracking coordinate system to obtain a transformation function further comprises:
receiving a position of the instrument relative to the tracking coordinate system at each of a plurality of fiducial markers;
identifying a corresponding position of each of the plurality of fiducial markers in at least one of the plurality of 2D projection images; and
performing a point-based algorithm based on the position of the instrument relative to the tracking coordinate system at each of the plurality of fiducial markers and the corresponding position of each of the plurality of fiducial markers in the at least one of the plurality of 2D projection images to obtain the transformation function.

6. The method of claim 1, wherein registering the plurality of 2D projection images relative to the tracking coordinate system to obtain a transformation function further comprises:
identifying a surface feature of the object relative to the tracking coordinate system;
identifying a corresponding surface feature of the object in at least one of the plurality of 2D projection images; and
performing a surface-matching algorithm based on the surface feature relative to the tracking coordinate system and the corresponding surface feature in the at least one of the plurality of 2D projection images to obtain the transformation function.

7. The method of claim 1, wherein registering the plurality of 2D projection images relative to the tracking coordinate system to obtain a transformation function further comprises:
identifying a volume feature of the object relative to the tracking coordinate system;
identifying a corresponding volume feature of the object in at least one of the plurality of 2D projection images; and
performing a volume-matching algorithm based on the volume feature relative to the tracking coordinate system and the corresponding volume feature of the object in at least one of the plurality of 2D projection images to obtain the transformation function.

8. The method of claim 1, wherein the object is a patient's organ that is subject to periodic movement.

9. The method of claim 1, wherein in response to detecting patient movement during the medical procedure, the method further comprising:
receiving a plurality of updated 2D projection images of the object at a plurality of projection angles during a third period of time;
registering the plurality of updated 2D projection images relative to the tracking coordinate system to obtain an updated transformation function that defines a relationship between a coordinate system of the plurality of updated 2D projection images and the tracking coordinate system;
continuously displaying the plurality of updated 2D projection images in an updated loop;
receiving an adjusted position of the instrument relative to the tracking coordinate system during a fourth period of time that is subsequent to the third period of time;
estimating an adjusted position of the instrument relative to the plurality of updated 2D projection images using the updated transformation function; and
displaying the estimated adjusted position of the instrument relative to the plurality of 2D projection images on the updated loop.

10. The method of claim 1, wherein registering the plurality of 2D projection images relative to the tracking coordinate system to obtain a transformation function further comprises:
creating a 3D model image of at least a portion of the object based on the plurality of 2D projection images;
registering the 3D model image relative to the tracking coordinate system to obtain a transformation function that defines a relationship between a coordinate system of the 3D model image and the tracking coordinate system, and wherein estimating an adjusted position of the instrument further comprises estimating an adjusted position of the instrument relative to the 3D model image using the transformation function, the method further comprising:
continuously displaying the 3D model image in a loop; and
displaying the estimated adjusted position of the instrument relative to the 3D model image on the loop.

11. The method of claim 1, wherein the plurality of 2D projection images are biplane fluoroscopic images or ultrasound images.

12. The method of claim 1, further comprising:
detecting the position of the instrument by sensing a change in a magnetic field; and
determining the position of the instrument relative to the tracking coordinate system of the magnetic field.

13. The method of claim 1, further comprising:
receiving a signal from the instrument at an optical sensor; and
determining the position of the instrument relative to the tracking coordinate system of the optical sensor.

14. The method of claim 1, wherein the instrument is a catheter.

15. The method of claim 14, wherein the medical procedure is an interventional cardiology procedure.

16. A guidance computing device for guiding an instrument during a medical procedure, comprising:
a display unit;
a processing unit; and
a memory in communication with the processing unit, the memory having computer-executable instruction stored thereon that, when executed by the processing unit, cause the processing unit to:

receive a plurality of 2D projection images of an object at a plurality of projection angles, the plurality of 2D projection images being recorded during a first period of time;

receive a position of the instrument relative to a tracking coordinate system during the first period of time;

register the plurality of 2D projection images relative to the tracking coordinate system to obtain a transformation function that defines a relationship between a coordinate system of the plurality of 2D projection images and the tracking coordinate system;

receive an adjusted position of the instrument relative to the tracking coordinate system during a second period of time that is subsequent to the first period of time; and estimate an adjusted position of the instrument relative to the plurality of 2D projection images using the transformation function.

17. The guidance computing device of claim 16, wherein the memory has further computer-executable instructions stored thereon that, when executed by the processing unit, cause the processing unit to:

continuously display the plurality of 2D projection images in a loop on the display unit; and display the estimated adjusted position of the instrument relative to the plurality of 2D projection images on the loop on the display unit.

18. The guidance computing device of claim 16, wherein the plurality of 2D projection images depict an actual position of the instrument relative to a patient's body during the first period of time.

19. The guidance computing device of claim 16, wherein the object is a patient's organ that is subject to periodic movement.

20. The guidance computing device of claim 16, wherein the plurality of 2D projection images are biplane fluoroscopic images or ultrasound images.

21. The guidance computing device of claim 16, wherein the instrument is a catheter.

22. The guidance computing device of claim 21, wherein the medical procedure is an interventional cardiology procedure.

23. A system for guiding an instrument during a medical procedure, comprising:

an imaging device configured to record a plurality of 2D projection images of an object at a plurality of projection angles, the plurality of 2D projection images being recorded during a first period of time;

an instrument tracking device configured to detect a position of the instrument relative to a tracking coordinate system; and a guidance computing device comprising:
  a display unit;
  a processing unit; and
  a memory in communication with the processing unit, the memory having computer-executable instruction stored thereon that, when executed by the processing unit, cause the processing unit to:
    receive the plurality of 2D projection images from the imaging device;
    receive the position of the instrument relative to the tracking coordinate system from the instrument tracking device during the first period of time;
    register the plurality of 2D projection images relative to the tracking coordinate system to obtain a transformation function that defines a relationship between a coordinate system of the plurality of 2D projection images and the tracking coordinate system;
    receive an adjusted position of the instrument relative to the tracking coordinate system during a second period of time that is subsequent to the first period of time; and
    estimate an adjusted position of the instrument relative to the plurality of 2D projection images using the transformation function.

24. The system of claim 23, wherein the memory has further computer-executable instructions stored thereon that, when executed by the processing unit, cause the processing unit to:

continuously display the plurality of 2D projection images in a loop on the display unit; and display the estimated adjusted position of the instrument relative to the plurality of 2D projection images on the loop on the display unit.

25. The system of claim 23, wherein the plurality of 2D projection images depict an actual position of the instrument relative to a patient's body during the first period of time.

26. The system of claim 23, wherein the object is a patient's organ that is subject to periodic movement.

27. The system of claim 23, wherein the imaging device is a biplane fluoroscopic device or an ultrasound device.

* * * * *